US008369592B2

(12) United States Patent
Leroy et al.

(10) Patent No.: US 8,369,592 B2
(45) Date of Patent: Feb. 5, 2013

(54) SYSTEM AND METHOD FOR IMAGING AND LOCATING PUNCTURES UNDER PROSTATIC ECHOGRAPHY

(75) Inventors: Antoine Leroy, Meylan (FR); Michaël Baumann, Grenoble (FR); Pierre Mozer, Vincennes (FR); Jocelyne Troccaz, Eybens (FR); Vincent Daanen, Meylan (FR)

(73) Assignees: Koelis, Grenoble (FR); Universite Joseph Fourier, Grenoble Cedex (FR)

( * ) Notice: Subject to any disclaimer, the term of this patent is extended or adjusted under 35 U.S.C. 154(b) by 269 days.

(21) Appl. No.: 12/678,795

(22) PCT Filed: Sep. 18, 2008

(86) PCT No.: PCT/FR2008/001306
§ 371 (c)(1),
(2), (4) Date: Dec. 13, 2010

(87) PCT Pub. No.: WO2009/071766
PCT Pub. Date: Jun. 11, 2009

(65) Prior Publication Data
US 2011/0081063 A1    Apr. 7, 2011

(30) Foreign Application Priority Data
Sep. 18, 2007  (FR) .................................... 07 06544

(51) Int. Cl.
*G06K 9/00*  (2006.01)

(52) U.S. Cl. ....................................................... 382/128

(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS
(Continued)

FOREIGN PATENT DOCUMENTS
EP    1 804 079    7/2007
WO    WO 2004/019799    3/2004
(Continued)

OTHER PUBLICATIONS

Phee, L et al.; "Ultrasound Guided Robotic System for Transperineal Biopsy of the Prostate;" Robotics and Automation, 2005, Proceedings of the 2005 IEEE International NAL Conference on, Barcelona, Spain, XP010871859, Apr. 18-22, 2005; pp. 1315-1320.

*Primary Examiner* — Atiba O Fitzpatrick
(74) *Attorney, Agent, or Firm* — Harness, Dickey & Pierce, P.L.C.

(57) ABSTRACT

The present disclosure relates to a prostatic imaging system including steps of recording and processing images acquired by the ultrasonographic head of a rectal probe equipped with an active puncture guide, characterized in that it includes steps of processing at least a part of the images acquired by the probe for calculating transformations to a "reference image" repository relative to the initial position of the prostate, at least a part of the images acquired during the successive punctures including the location of the various positions of the needle being recorded with a view to visualising representations thereof on a single image including at least a part of the prostate. The present disclosure also relates to a system for the prostatic imaging implementing said prostatic imaging method.

26 Claims, 9 Drawing Sheets

U.S. PATENT DOCUMENTS

| | | |
|---|---|---|
| 5,447,154 A | 9/1995 | Cinquin et al. |
| 6,932,089 B1 | 8/2005 | Cinquin et al. |
| 2003/0135115 A1* | 7/2003 | Burdette et al. .............. 600/437 |
| 2006/0173290 A1 | 8/2006 | Levallee et al. |
| 2007/0270687 A1* | 11/2007 | Gardi et al. .................. 600/425 |
| 2009/0093715 A1* | 4/2009 | Downey et al. ............... 600/437 |
| 2010/0324419 A1* | 12/2010 | Gardi et al. .................. 600/443 |

FOREIGN PATENT DOCUMENTS

WO    WO 2006/089426    8/2006

\* cited by examiner

SYSTEM AND METHOD FOR IMAGING AND LOCATING PUNCTURES UNDER PROSTATIC ECHOGRAPHY

CROSS-REFERENCE TO RELATED APPLICATIONS

This application is a National Phase Entry of International Application No. PCT/FR2008/001306, filed on Sep. 18, 2008, which claims priority to French application Ser. No. 07/06544, filed on Sep. 18, 2007, both of which are incorporated by reference herein.

FIELD OF THE INVENTION

The present invention relates to the field of the methods and equipment intended for the computer-aided diagnosis and therapeutic treatment applied to prostate pathologies and more particularly cancer. It more precisely relates to a method and a system for locating in vivo biological samplings done using a transrectal ultrasonographic probe.

BACKGROUND

Prostate punctures, more particularly needle-biopsies, are carried out in a standard way through a transrectal ultrasonography. The ultrasonographic probe includes a puncture guide mechanically positioned so that the path of the puncture needle is in a/the sagittal acquisition plane of the probe. The positioning of the needle with respect to the organ is made through a visual guiding more particularly using the ultrasonographic pictures of said acquisition plane. For a 3D probe, "sagittal plane" will mean the probe "field of view" and, if need be, the mid-plane of the field of view.

In the case of the needle-biopsy, to carry out analyses, the practitioner will comply with a pre-defined puncture scheme of at least six punctures, with twelve being the standard. From this scheme, he/she must distribute the sampling in a homogenous way in the prostate area opposite the rectal probe head to optimise the chances of detecting a possible tumoral focus. The main difficulty consists in making a coherent distribution of the puncture points which can be optimum as regards the first diagnostic results on an organ which is not directly visible to an operator, which is not immobilized and which is deformed during the operation. The handling of the probe head thus requires both great skills and a strong experience to guarantee that the actual point of the sampling will match that on the scheduled puncture scheme.

This difficulty in guiding the puncture head to a theoretical target a fortiori implies the practitioner failing to know the exact position of the sampling carried out. This lack of information may lead to an incorrect diagnosis which is useless and also to repeated biopsies or to a non-focussed or at least a non-optimal therapy. The information on the intra-prostatic location of the puncture head is the key of a system for efficiently and globally treating prostatic pathologies and more particularly cancer.

International Application WO2005/110255

The international application WO2005/110255 provides for a solution for the targeting and the biopsy of tissues for medical purposes, and more particularly a targeted biopsy system, which enables the planning of the tissue to be sampled, the targeting of specific areas of the tissues, with reference to the plane, the capture of the tissue sample and the recording the source location of the tissue sample. The system is more particularly used for collecting samples of tissues from the prostate gland. It includes a flexible biopsy needle, a directional guide for said biopsy needle, imaging means, a biopsy scheme and recording means.

Drawbacks of Such Solution WO2005/110255

The problem entailed in this solution is that the identification of the prostate on the image is purely mechanical. Therefore, the image of the needle with respect to the prostate is calculated using a succession of references:

the "operation room" reference which makes it possible to determine the position of the probe using the support;

the "patient's body" reference which is likely to move with respect to the "operation room" reference;

the "organ" reference which is liable to move and be deformed with respect to the "patient's body" reference;

the "probe" reference which is theoretically stationary with respect to the "operation room" reference, but the mechanical connections are not absolutely rigid and thus lead to a possible shifting.

The image of the probe with respect to the prostate is thus calculated with an accumulation, or rather a multiplication of uncertainties and leads to localising the probe with respect to the prostate with several millimeters' inaccuracy. Therefore, the position of the sample with respect to the gland cannot be recorded nor used. Consequences are significant: the tumoral area is known only within several millimeters' accuracy, which entails treatments on needlessly large areas. Under these conditions, a therapeutic treatment, for example by local irradiation, cannot be focused on the tumoral area.

International Application WO2004/019799

From the international application WO2004/019799 is also known, in the prior art, a method to determine the position of a biopsy needle within a target volume, said target volume being defined as a space inside a patient. The method consists in:

generating several images of the target volume, spatially recording the images for generating a three-dimensional representation of the target volume from the recorded images, determining the location of the biopsy needle in the three-dimensional representation of the target volume, and correlating the determined biopsy needle location with the spatially recorded images.

The graphic of the target volume includes a graphic representation of the determined location of the biopsy needle. This document also describes a locating technique wherein a camera tracking a reference target is fixed to an ultrasonographic probe, which enables an accurate localisation of the probe in a coordinate system. However, in the solution described in this document, the space inside the patient is not precisely defined: it can be interpreted as an assembly of tissues belonging to a patient or as a volume, the position and orientation of which are defined with respect to a coordinate system outside the patient.

In the first case, the system determines the position of the needle with respect to the patient's anatomy, whereas in the second case, the system determines the position of the needle with respect to a reference system outside the patient. In the second case, it is essential that the patient and the targeted organ do not move and are not deformed during the operation, or the position of the needle calculated in the targeted volume will not match the position of the needle with respect to the patient's anatomy.

It is clear, with the encapsulating volume and the reference system x-y-z as shown in FIG. 1 of such international application, as well as with the description of the locating methods (D1, p. 13 1.24-p. 14 1.35) that the system provided is in the second case. Several methods are provided, which all aim at localising the position of the ultrasonographic image with respect to an external and thus non-anatomic reference. The first method (D1, p. 13, 1.24-37) is stereotactic and localises the images with respect to the camera reference system. The second method is acoustic (D1, p. 13, 1.38-p. 14) and localises the images with respect to the pinger reference.

The third method provided (D1, p. 14, 1.5-1.35) is mechanical and thus consists in fixing the path of the needle using a guide with respect to the probe, and in immobilizing the prostate at the same time with a pawl to reduce the mobility thereof, and in determining the position of the probe (and thus of the needle) with a mechanical system (e.g. an encoded articulated arm), the identification for such system. The pawl makes it possible to reduce the movement of the prostate resulting from the movement of the probe but it cannot make up for the patient's motions (as he or she is locally anesthetised). As a summary, the system provided in the prior art document is capable of determining the needle with respect to an identification system inside the patient and thus requires that the targeted tissues do not move during the operation to obtain clinically satisfactory results.

Drawbacks of Such Solution WO2004/019799 and Solution Provided by the Invention

The claimed invention is based on a method for localising the needle with respect to an anatomic identification system, the latter being defined by a 3D reference image containing the targeted anatomy, i.e. the prostate. The matching of imaged tissues in the tracking images and reference images makes it possible to be independent of external localising systems such as those described in the international application WO2004/019799. The invention thus makes it possible to manage the "jumps" of patients which are well-known to the practitioners and which result from the pains caused upon the triggering of the biopsy gun, thanks to the utilisation of a purely anatomic identification system.

Patients jump approximately in 10 to 20% of transrectal prostate biopsies operations. The invention also makes it possible to avoid problems relative to the motions of the prostate more particularly resulting from the motions of the endorectal probe. The document WO2004/019799 does not provide the exploitation of one of the acquired images in order to determine the "reference image" relating to the initial position of the prostate.

The method provided in this document also aims at the same goal, but it implements a totally different means: it makes it possible to equip the external part of the probe with a camera which records the image of a pattern outside the patient and used for resetting the position of the probe. The part of the probe which remains outside the patient's body is provided with a camera which must be oriented to a stationary pattern for example glued on a wall of the operating block or the equipment supporting the patient.

The drawbacks of such solution are multiple:

it imparts constraints which are an obstacle to ergonomics and operation of the probe, it provides an external reference in the operating block and not directly connected with the observation area, i.e. the prostate itself, it does not make it possible to prevent the interferences resulting from the patient's untimely motions.

it implies the passage through a succession of references degrading the precision of the transformations:

"Operating block/patient's body" transformation,

"Operation room/prostate" transformation.

This document thus does not disclose the claimed characteristics and does not suggest these obviously for the persons skilled in the art.

International Application WO2006/089426

This document relates to a system and a method for performing a biopsy of a target volume and a computer device for planning the same. An ultrasonic transducer captures ultrasound volume data from the target volume. A three-dimensional recording module records the ultrasound volume data with supplementary volume data relative to the target volume. A biopsy planning module processes the ultrasound volume data and a supplementary volume data in combination in order to develop a biopsy plane for the target volume. A biopsy needle biopsies the target volume in accordance with the biopsy plane. A solution consisting in injecting a pre-operational "additional" image, on a per-operational "probing" image used for guiding a practitioner's gestures (§46 p. 13). The approach claimed in the present invention is different in that it aims at localising the organ during the punctures, with respect to a reference position.

The system described in the document WO2006/089426 also uses the localising of the images in a non-anatomic and external reference system to determine the position of the needle in the reference volume (FIG. 4, 108 and p. 22, 1.8-121 and §64 p. 16 with the support and MCM). The "three-dimensional" ultrasonography obtained with this method (FIG. 7, FIG. 8, FIG. 4 132, §139 p. 11) is different from the actual 3D ultrasonography on which an advantageous variant of the present claimed invention is based, as regards the quantity of available data, speed, collision and fineness of the 3D anatomic reconstruction. The system provided in the document WO2006/089426 is thus exposed to the same defects as those identified for the system disclosed in the document WO2004/019799. More particularly, the movements of the organ and, a fortiori, of the patient disturb the whole guiding method.

SUMMARY

The aim of the invention is thus to remedy such drawbacks while providing a solution making it possible to improve the precision of the biological samplings and the localising of corresponding test specimens. In addition, the solution brought by the present invention makes it possible:

prior to the operation, to define a puncture planning which can be transferred to the per-operational time by resetting the data;

at the per-operational level, to guide the needle and visualise the spatial distribution of the already done punctures;

after the operation to visualise the spatial distribution of the punctures done; in the case of the biopsy, this is the distribution of the samples and the tumoral tissue identified during an anatomopathological analysis to make a diagnosis and help the planning of a focused treatment.

The guiding of the per-operational needle and the precise identification of the puncture sites, made possible by the invention, makes a focused post-operational treatment possible. For this purpose, the invention in its broadest sense also relates to a prostatic imaging method including steps of recording and processing images acquired by the ultrasonographic head of a rectal probe provided with an active puncture guide, characterised in that it includes steps of processing at least a part of the images acquired by the probe to calculate the transformations to a "reference image" repository relative to the initial position of the prostate, at least a part of the images acquired during the successive punctures including the localising of the various positions of the needle being recorded with a view to visualising the representations thereof on a single picture including at least a part of the prostate.

In a particular embodiment, the position of the sampling needle is visualised in the "reference image" repository or the "tracking image" repository after puncture, superimposed on an image of at least a part of the prostate showing the various positions of the prior samplings. In another particular embodiment, the performed or theoretical position of the sampling needle is visualised in real time in the "reference image" repository or "tracking image" repository, being superimposed on an image of at least a part of the prostate showing the various positions of the prior samplings. In another particular embodiment, the distribution of the tumoral tissue is visualised in the "reference image" repository after merging the distribution of marked punctures with the results from the anatomopathologic analysis. Preferably, the invention includes the steps of recalculating a new prostatic marked image at each sampling.

According to an advantageous variant, the refreshing frequency of the images acquired by the ultrasonographic probe is of at least 3 pictures per second. According to an advantageous alternative, a flow of images is acquired, the periodicity of which depends on the refreshing frequency of ultrasonographic images, the speed of transfer to the computer and the processing speed of received images. According to a first exemplary implementation, the ultrasonographic probe gives a three-dimensional imaging. According to a second exemplary implementation, the ultrasonographic probe gives a "2.5 dimensional" type imaging (2D images localised in space). Preferably, the imaging method according to the invention includes a step of chronological marking with a serial number implementing univocal labelling means for each sampling area.

According to a first exemplary embodiment, the univocal labelling means are manually generated when the needle is in position. According to a second exemplary embodiment, the univocal labelling means are generated by triggering the manual data acquisition or automatic data acquisition through the capture of a sound, light, magnetic or tactile signal at the very moment of a biopsy sampling.

In a particular embodiment, the step of processing the acquired images further implements a kinematic model derived from the anatomic constraints which are specific to a transrectal puncture of the prostate thus making it possible to identify probable positions of the probe during the operation. In a particular embodiment, the step of processing the acquired images further implements a process of pre-calculating the probable positions of the probe during the biopsy and images corresponding to the pre-calculated positions of the probe from the reference image. Advantageously, the step of processing the acquired images further implements an image resetting algorithm based on the local optimisation of a measure of the similarity.

The invention also relates to a prostatic imaging system including a rectal probe and a calculator, the probe including an ultrasonographic head for taking an image of the punctured area done with a needle actuated by the operator or automatically, with the calculator including means for recording and processing of images acquired by said ultrasonographic head, characterised in that the computer includes means for the recording and processing of the images acquired by the probe to calculate transformations to a "reference image" repository relative to the initial position of the prostate, at least a part of the images acquired during the successive punctures including the localising of the various positions of the needle being recorded with a view to visualising the representations thereof on a single image including at least a part of the prostate. Preferably, the system further includes a receptacle for the collection of tissue samples with an identifier correlated with the marking of the corresponding sampling area of the single image of the marked prostate. Advantageously, the system integrates a system for creating labels to be applied onto the receptacle bearing the above-mentioned single identifiers. The editing system can be composed by a thermal printing machine or an inkjet printing machine, adding a barcode or a matrix code.

According to a first exemplary embodiment, the rectal probe is a manually operated probe without any robotised positioning. According to a second embodiment, the rectal probe is a manually operated probe actuated by an optical or magnetic locator. According to a third exemplary embodiment, the rectal probe is a robotised-positioning probe. The invention also relates to a computer medium including the recording of a calculator control programme, for the implementation of the above-mentioned method.

BRIEF DESCRIPTION OF THE DRAWINGS

The invention will be better understood when reading the following description relating to a non-limitative exemplary embodiment, wherein.

DETAILED DESCRIPTION

The present exemplary embodiment relates to a system implementing a medical imaging method enabling the acquisition and analysis of 3D ultrasonographic images with a view to localising samples or needles with respect to the prostate. Images resetting algorithm for the statistical analysis of similarities enables the matching of all the acquisitions in the same repository relative to the organ.

Prior to the operation, a graphic interface makes it possible for the clinician to plan a diagram of punctures on a first ultrasonographic acquisition. Several options are offered:

a manual planning without any constraint;

an equally distributed automatic planning for a defined number of samples with possible manual corrections, afterwards;

a differential planning, i.e. the visualisation of the previous punctures superimposed on the actual acquisition in case of repeated operations;

the transfer of a planning carried out on an external imaging for example of the MRI type.

The system can be used and the method implemented according to three embodiments:

prior to the operation, the system can, after each puncture, show in a view which is annexed to the real time ultrasonography, the position of the samplings carried out so far during the operation. For each puncture, the 3D ultrasonographic acquisition can be either manual or automatic through a, for example sound detector. This embodiment will be called "consultation during the operation".

during the operation, if the computer equipment enables it, the system can represent in real time on the ultrasonographic guiding image or on a model, the actual position of the puncture guide with respect to the organ. This mode of utilisation can be added to the preceding one. The real time tracking coherent with the position of the organ is provided by the resetting algorithm of the present invention; however, it can rest on location information supplied by an external (optical, magnetic, etc.) locator. This embodiment will be called "guiding during the operation".

after the operation, the system offers the clinician a 3D visualisation of the punctures carried out with, if need be, a quantitative comparison with a prior operation, for quality purposes. The post-operation information on the distribution of tissue samples makes it possible, together with the results of the anatomopathological analysis, to precisely show the tumoral areas with respect to the prostatic volume. Such information which is useful for the diagnosis can be shared and transmitted to the therapist, which will have the possibility of focusing the treatment.

Figure 1:
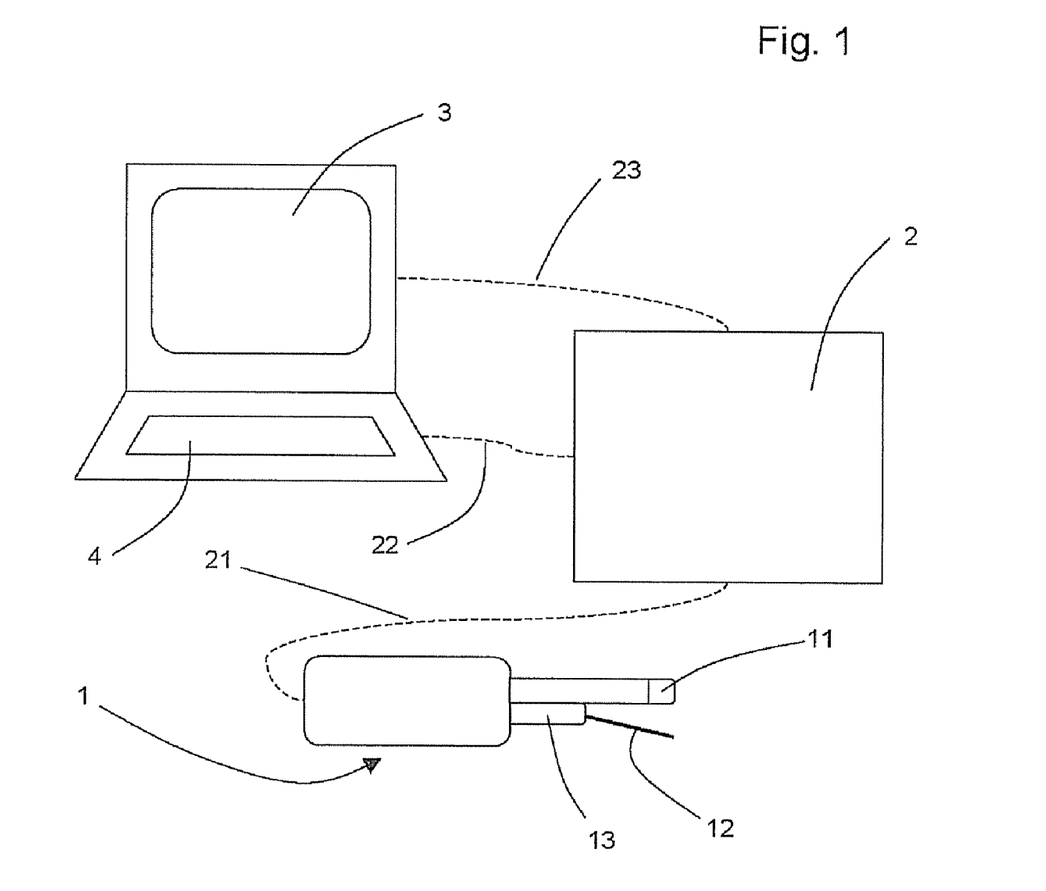
FIG. 1 is a diagram of the prostatic imaging system.

The system is composed of various elements as illustrated in FIG. 1. A rectal probe 1 makes it possible to position precisely a core drilling needle 12. As a matter of fact, a core drilling needle 12 is integral with the rectal probe 1. It is liable to take two positions: a first position where said needle 12 is located inside a guide integral with said rectal probe 1 when no core drilling is in progress and a second position where said needle 12 is located outside said rectal probe 1 when the coring is in progress so as to sample some biological tissue.

An ultrasonographic head 11 is positioned at the end of the rectal probe so that the position of said rectal probe with respect to the prostate not visible during the handling of said rectal probe 1 can be observed on a monitor 3 via a system for the acquisition and analysis of images 2. The probe can also be composed of a side or oblique sight 3D probe. Said ultrasonographic head 11 is a 3D ultrasonographic head. In a particular embodiment, said ultrasonographic head is a "2.5-dimensional" type imaging ultrasonographic head. Said "2.5-dimensional" type imaging is defined as an image system implementing spatially localised 2D images. In an advantageous variant, the ultrasonographic head 11 is provided with an optical or magnetic marker capable of communicating with an optical or magnetic locator so as to make the tracking in real time easier.

A monitor 3 makes it possible to visualise the flow of images acquired by the ultrasonographic head 11. The visualisation of the flow is operated at the refreshing rate of images acquisition and analysis system 2. Said monitor 3, or in a particular variant, a second monitor, makes it possible to simultaneously visualise the "reference image" repository or the "tracking image" repository which may include the planned puncture paths, the presently targeted path and the previous paths. The refreshing rate of said visualisation of the "reference image" repository or the "tracking image" repository depends on the performances of the image acquisition and analysis system 2. Said visualisation makes it possible for the clinician to observe the position of the rectal probe 1 with respect to the organ and/or to observe the sampling area actually punctured after the triggering of a core drilling.

A control table 4 makes it possible for the clinician to carry out the various adjustments required for the correct execution of a biopsy scheme. More particularly, it is possible to control the establishment of a biopsy planning to choose the way the sampling targets are identified systematically through a differential calculation, from an external image or manually, and to choose the fineness of the calculations upon the processing of the images. Advantageously, said monitor 3 is a touch screen displaying virtual graphic objects corresponding to at least a part of said control table 4 or any other control table.

A gun 13 makes it possible to perform core drilling. As a matter of fact, it is provided with a (not visible) actuator and mechanically connected to the core drilling needle 12 so that the triggering of the actuator by the clinician causes the request for the acquisition of an image by the ultrasonographic head 11 during the next period of the imaging method. In an advantageous variant, the ultrasonographic head 11 and the gun 13 are in a triggering mode without any contact for the automatic acquisition of ultrasonographic images upon the core drilling. A (non-visible) receptacle is provided for the collection of the sample tissues, with an identifier correlated with the marking of the corresponding sampling area on the single image of the marked prostate.

A sample marking device or labelling device is used so that each sampling area can be identified univocally. The labelling means implemented are generated in a chronological order of the biopsies performed, whatever said chronological order selected by the clinician, without the cohesion of the results being affected. As a matter of fact, the system is not sensitive to a discrepancy between the spatial distribution and the chronological order of biopsies, since with each sampling is associated an image which cannot be confused with the image associated with another sampling.

In a particular embodiment, the labelling means are manually generated when the core drilling needle is positioned. In another particular embodiment, the univocal labelling means are generated by an automatic triggering of data acquisition for the capture of the sound, light, magnetic or tactile signal at the very moment of the biopsy.

The image acquisition and analysis system 2 is a system capable of communicating through communication channels 21, 22, 23, in addition with the ultrasonographic head 11 for the control of image acquisitions, with the control table 4 for the adjustment by the clinician, and with the monitor 3 for the visualisation of the processed images. Said images acquisition and analysis system 2 includes a (not visible) computer medium making it possible on the one hand to record the acquired images and on the other hand to record beforehand the control programme of a (not visible) calculator for implementing methods for processing acquired and recorded images and methods for estimating core drilling needle position with respect to a biopsy planning. Said images acquisition and analysis system 2 further comprises a (not visible) ultrasonographic system enabling the acquisition of images and the transfer thereof to the above-mentioned computer medium.

The method for processing acquired and registered images further implements an image resetting algorithm based on the optimisation of a similarity measurement, from the global optimisation, from positions supplied by a kinematic model and followed by one or several local optimisations. A pre-calculation step of the positions of the model and corresponding images makes it possible to decisively accelerate the global optimisation.

Figure 2:
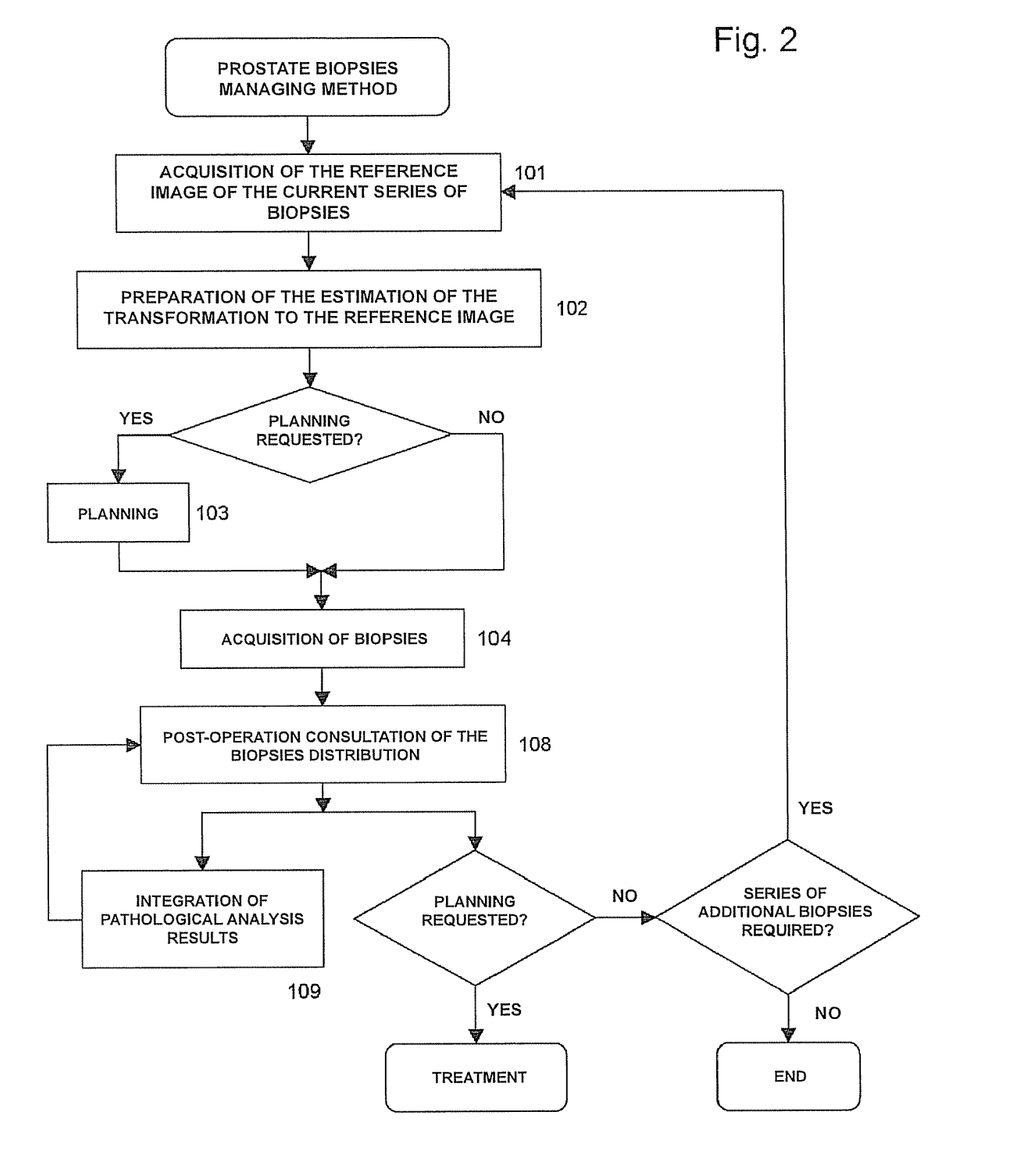
FIG. 2 is a diagram of the management procedure of the prostate biopsies.

The procedure of management of biopsies is illustrated in FIG. 2. Such procedure mainly has two steps:

a preliminary sequence including the acquisition of reference image 101, the preparation of the estimation of the transformation to the reference image step 102 and possibly the preparation of the sampling planning step 103; and a sequence of sampling collection.

Such steps are successive with the patient remaining on the operation table and the various sequences being performed during the same operation without the patient's significant motion for a single biopsy sequence, the duration of which is of a few dozens of minutes. The time between the acquisition of the reference image and the performance of samplings can be from a few seconds to a few minutes.

The preliminary sequence starts with the acquisition of the reference image of the current biopsy series 101. Said reference image is defined as the entire image of the prostate, acquired by the image acquisition and analysis system 2 during the preliminary time, prior to the handling of the system by the clinician.

Such reference image acquisitions step consists in acquiring one or several adjacent ultrasonographic images for example three images in the example described, with the ultrasonographic probe, the practitioner modifying the orientation of the probe head between each acquisition to obtain three distinct images of the prostate. Such three images are obtained by the application of a processing on these three digital images so as to recalculate the single image, also called "reference image" corresponding to a three-dimensional view of the whole of the prostate. Each one of the initial images generally covers only a part of the prostate and the combination of the images taken along slightly different angles makes it possible to reconstruct an image of the whole prostate as it is, the positioning and the configuration of the prostate and of the patient corresponding to the acquisition sequencing coming very shortly prior to the sampling sequencing. This "reference image" is acquired with the same equipment and under the same conditions as the images which will then be required during the sampling steps.

Such reference image is used for preparing the successive positions of the rectal probe 1 based on the biopsy scheme. From said reference image, the computer makes a step of preparing the estimation of the transformation to the reference image 102. Such step of pre-calculation makes it possible to pre-estimate the probable positions of the probe and the images corresponding to this position. It requires several steps which will be described hereinunder and illustrated in FIG. 7. The clinician also can choose between the drawing up of a planning 103 or not. The planning makes it possible to position a distribution card with one or several series of biopsies thus facilitating his or her work during the acquisition of biopsies 104. The step of drawing such planning will be described hereinafter and illustrated in FIG. 3. As the ultrasonographic probe is guided 1, the images of the various sampling areas corresponding to the possible planning 103 for the biopsy are acquired and stored on the computer medium of the images acquisition and analysis system 2. The result of the acquisition of biopsies 104 having been obtained, the practitioner can carry out a post-operational consultation of the distribution of biopsies 108, in combination with the integration of an anatomopathological analysis 109 so as to establish whether a treatment is recommended or if a new series of additional biopsies is required or if the patient has no pathology as regards the prostate.

Figure 3:
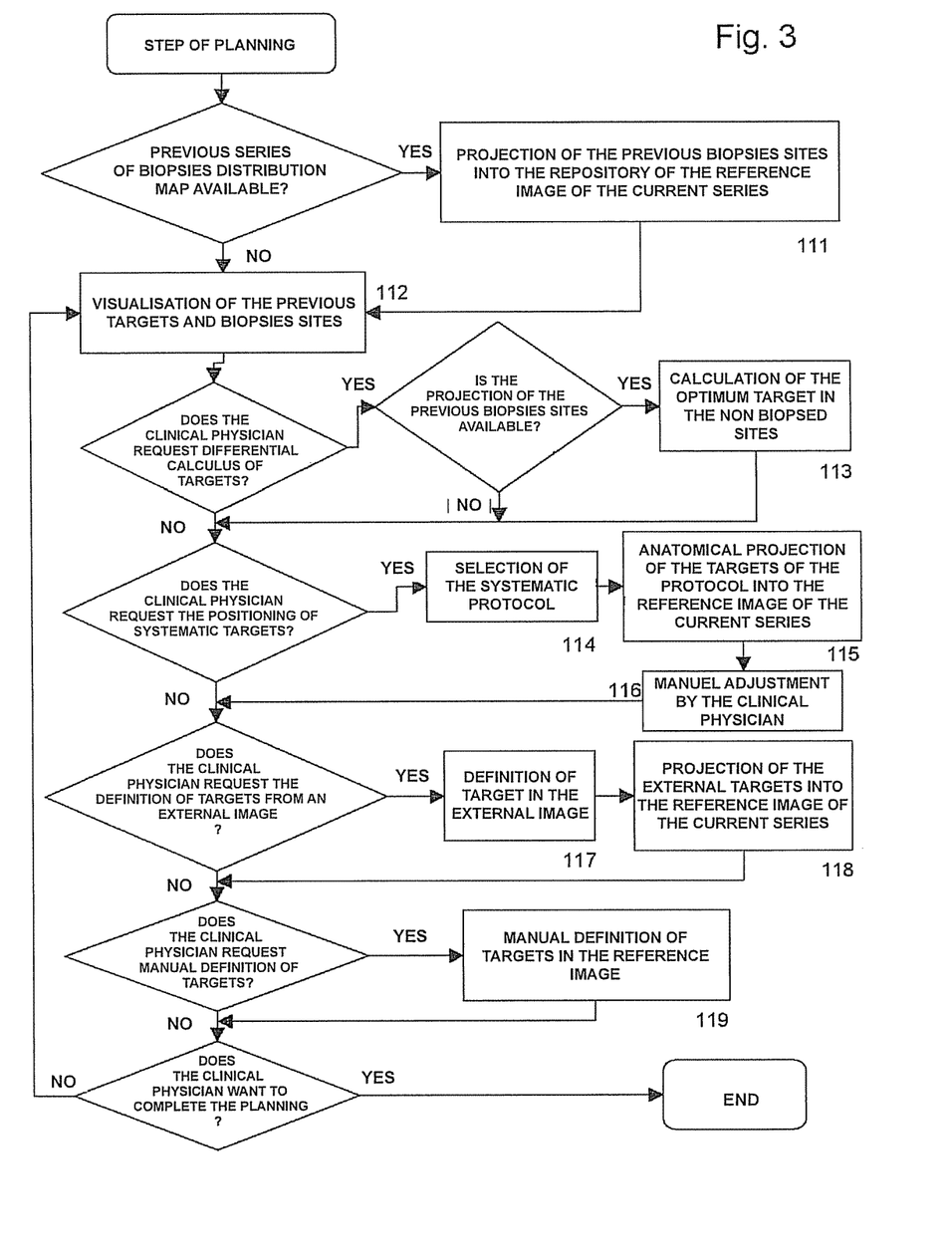
FIG. 3 is a diagram of the procedure of creation of a biopsy planning.

The procedure for drawing up the planning 103 for the biopsy is illustrated in FIG. 3. If maps showing the distribution of one or several series of previous biopsies for the same patient are available, the computer makes a projection of the previous sites of biopsies in the reference image of the current series 111. The practitioner can have access to the visualisation of targets and previous sites of biopsy 112 through the visualisation screen 3. The clinician has the possibility of choosing then the drawing of the biopsy planning according to four distinct modes. If the clinician requests a differential preparation of optimal sampling targets and if projections of biopsy sites beforehand are available, the calculator calculates the optimum targets in the non-biopsied sites 113. If the clinician requests the positioning of systematic targets at N samples, with N being a parameter defined beforehand by said clinician, the calculator selects the systematic protocol 114, then the anatomic projection of the targets into the reference image of the current series 115, the manual adjustment 116 being then manually carried out by the clinician. If the clinician requests the definition of targets from an image having a modality which is not an ultrasonographic external image obtained for example by a MRI, the calculator defines the target in the external image 117 and then it projects external targets into the reference image of the current series 118 by a multi-modal matching. Finally, if the clinician requests the manual definition of targets, he/she will carry out said manual definition of targets in the reference image 119. Finally, if the clinician considers that the planning is not completed, the following steps will thus consist again in visualising targets and biopsy sites beforehand 112 with, again the same possible selection available to the clinician. If not so, the step of drawing up the planning 103 of biopsy is completed.

The step of acquisition of biopsies 104 can be carried out in three variants, as a function of the ultrasonographic system and the computer device used. The first variant also called "guiding during the operation" 105 requires a real time flow of 3D ultrasonographic images making it possible to identify and visualise at any time the position of the current puncture path. Such variant makes it possible to guide this probe insofar as the image is acquired and refreshed at a rate of more than 3 images per second. The guiding of the probe by the clinician is thus facilitated, and thus the identification in real time of the next puncture site. On the contrary, as the acquisition of the image is not carried out at the precise moment when a biopsy is triggered, the acquired and recorded image not exactly corresponds to the sampling made at the moment of the sampling. Advantageously, a sound, light, magnetic or tactile system for detecting the biopsy can help synchronising the tracking image with the biopsy. In the second variant also called the "consultation during the operation" 106, the acquisition and transfer of a 3D image occurs only after the acquisition of biopsy thus eliminating the required real time flow but supplying an immediate per-operational return on the puncture path. If the computer system makes it possible, said first variant and said second variant can be added. Finally, the third variant also called "post-operational consultation" 107 simply uses the recording of 3D images in per-operational time and only estimates the puncture paths after the operation.

Figure 4:
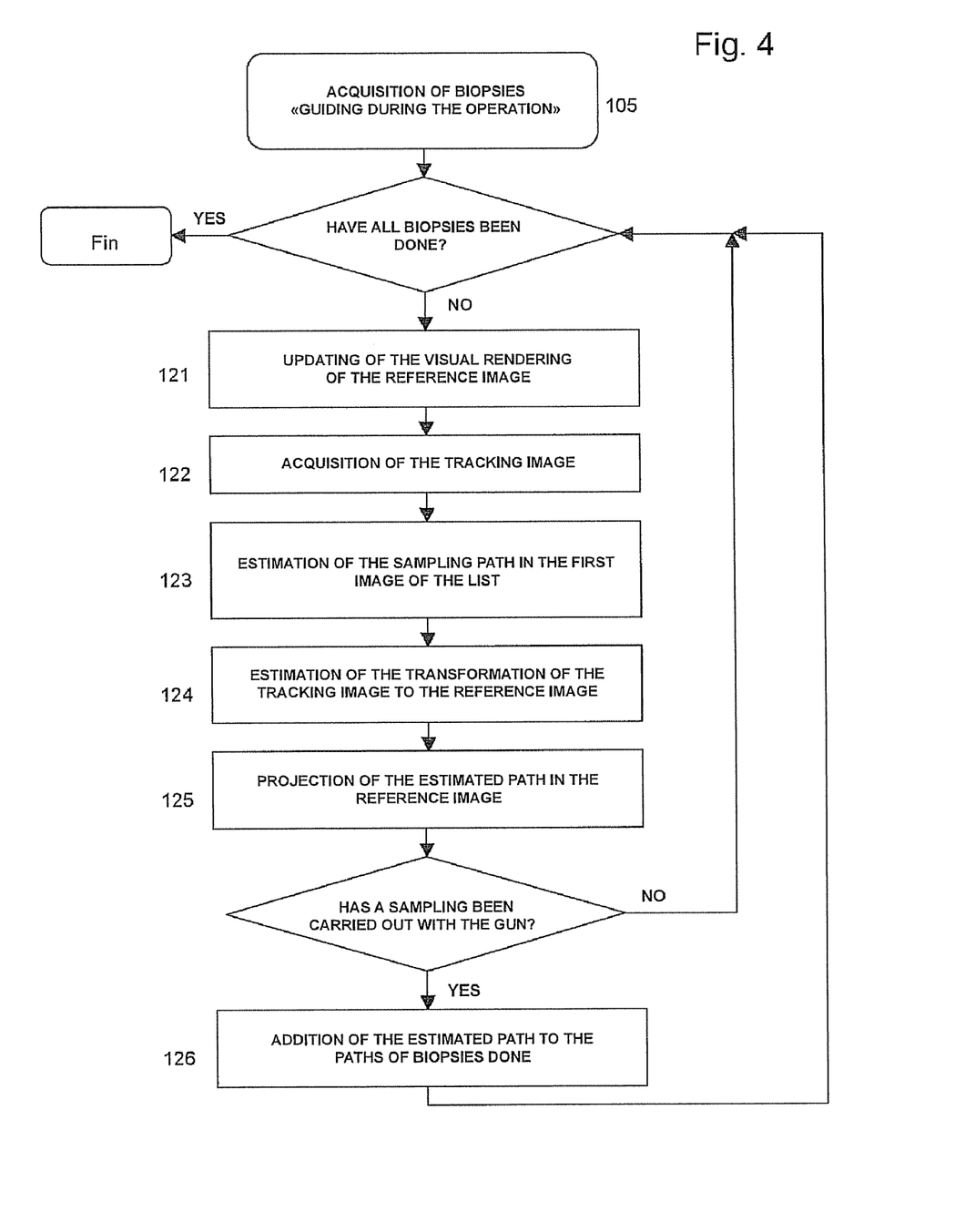
FIG. 4 is a diagram of a variant of biopsies acquisition method, also called "consultation during the operation"

In the first variant also called the "guiding during the operation" 105 and illustrated by FIG. 4, the acquisition of the tracking image 122 is performed independently of a gun. Such tracking image is defined as the image acquired by the acquisition and analysis system for images during the handling of the system by the clinician. The system can show in real time, on the guiding ultrasonographic image or on a model, the current position of the puncture guide with respect to the organ. The real time tracking in cohesion with the position of the organ is provided by the resetting algorithm of the present invention; it can however rest on location information supplied by an optical, magnetic, mechanical or robotic external locator. If all the biopsies are carried out, such procedure is completed. If not all the biopsies have been completed, a method composed of a succession of the steps 121 to 125 is carried out so as to actualise the data of the device and to acquire a new image at the rate of at least 3 images per second. The first step consists in the updating of the visual rendering of the reference image 121 including the biopsies completed paths, planned biopsy paths and the estimation of the sampling path. It makes it possible for the clinician to observe on the visualisation screen 3 the reference image with the information required for the guiding of the rectal probe 1. The method then implements a succession of the steps 122 to 125, so as to carry out the acquisition and processing of the images. This succession of steps includes the acquisition of the tracking image 122 by the imaging device 2. The calculator then carries out an estimation of the sampling path in the first image of the list 123. Then the method implements the estimation of the transformation of the tracking image to the reference image 124. This estimation implements the calculation algorithm and will be better illustrated in FIG. 9. The calculator finally projects the estimated path in the reference image 125. If during such succession of steps no sampling is carried out with the gun and if all the biopsies have not been completed, the procedure repeats the steps 212 to 125. If, on the contrary, a sampling has been carried out with the gun during the time between two refreshing operations, then the imaging device 2 will add the estimated path to the completed biopsy path 126. If, when considering this added path all the biopsies have been completed, the procedure is completed. If not so, the steps 121 to 125 are repeated.

Figure 5:
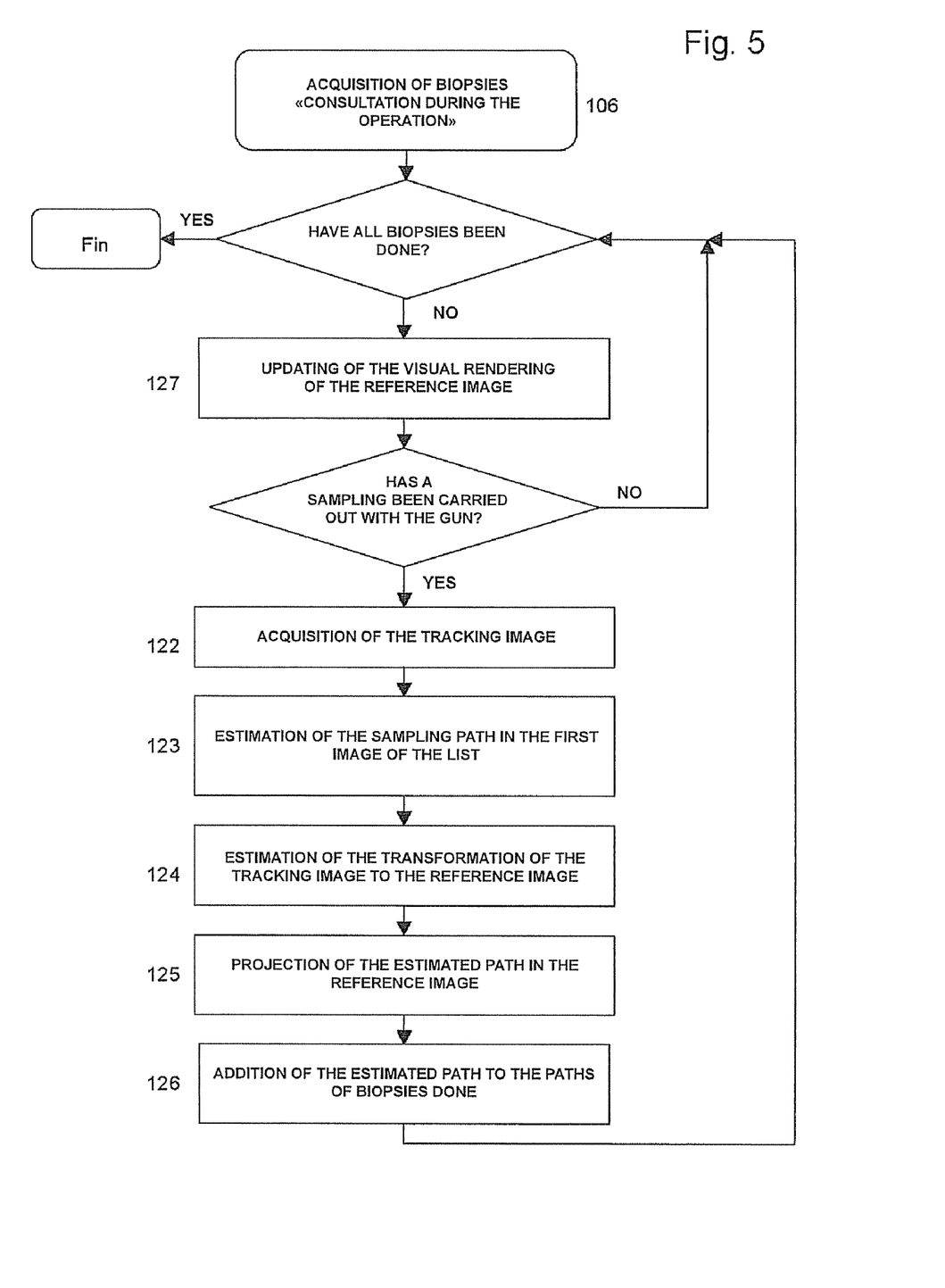
FIG. 5 is a diagram of a variant of biopsies acquisition method, also called "guiding during the operation"

In the second variant also called the "consultation during the operation" 106 and illustrated in FIG. 5, the acquisition of the tracking image 122 is triggered by a gun. The system can, after each puncture, show on an appended view the ultrasonographic image in real time, with the position of the samples carried out so far during the operation. If all biopsies are completed, this procedure is completed. If all biopsies have not been carried out, the first step consists in the updating of the visual rendering of the reference image 127. This step includes the completed biopsy path and the planned biopsy path. As long as a sampling is not triggered, the system carries out only step 121. When a sampling is triggered, the method implements a succession of the steps 122 to 126, so that the acquisition and the recording of the image is carried out. Such steps 122 to 126 are identical to the steps 122 to 126 described in the first variant also called "guiding during the operation" (FIG. 4). If, considering the new added path, all biopsies have been complied, the procedure is over. If not so, the step 121 is repeated in a cycle, so long as a new sampling is not triggered. It should be noted that in such second variant, the user can control a tracking image prior to the biopsy so as to visualise a reliable estimation of the current place aimed at by the gun.

Figure 6:
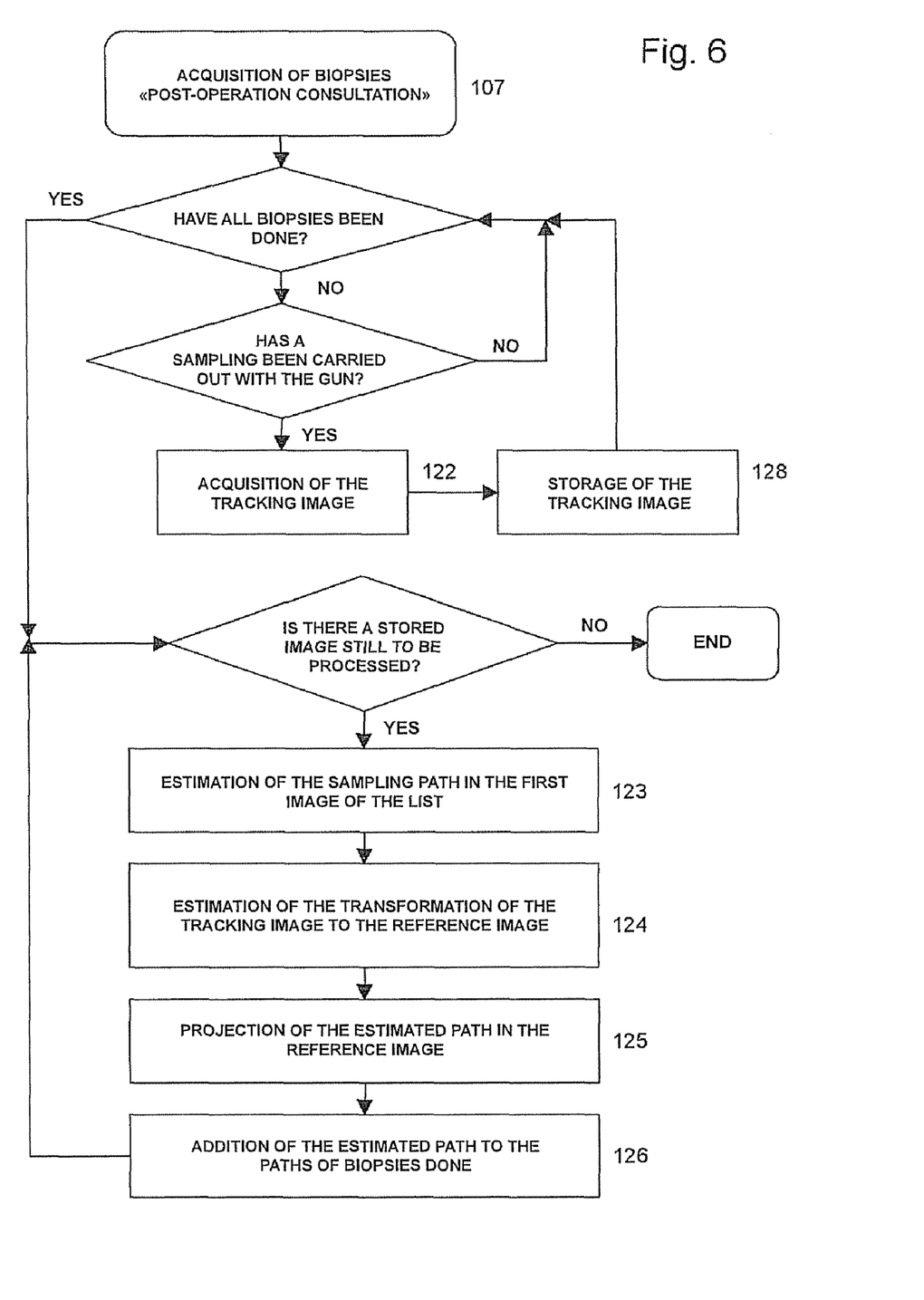
FIG. 6 is a diagram of a variant of biopsies acquisition method, also called "post-operational consultation"

In the third variant also called "consultation after the operation" 107 and illustrated in FIG. 6, the processing is carried out after the operation. So long as all biopsies are not acquired, at each sampling carried out with the gun the method implements the step of acquisition of the tracking image 122, then a step of storing said acquired tracking image 128. If, on the contrary, all the biopsies have been acquired, and so long as there is still a stored image to be processed, the steps 123, 124, 125 and 126 such as defined for the procedure also called the "guiding during the operation" are implemented so as to process the stored images.

Figure 7:
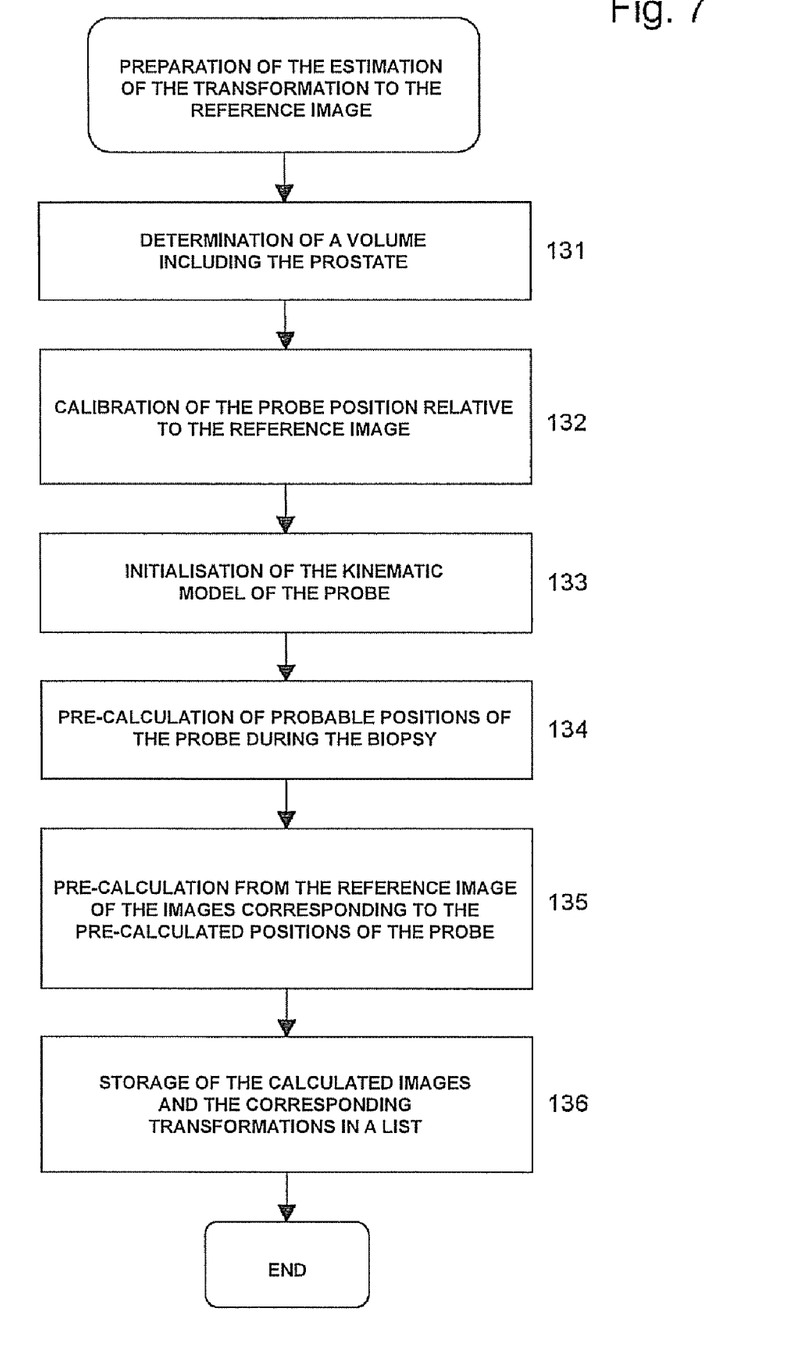
FIG. 7 is a diagram of the method for preparing the estimation of transformations to the reference image.

The method of preparation of the estimation of the transformation to the reference image 102, implemented prior to the possible drawing up of a planning 103, is illustrated in FIG. 7. The first step consists in determining a volume surrounding the prostate 131. The position of the probe is then calibrated with respect to the reference image 132. The kinematic model is initialised 133. Then the calculator pre-calculates probable positions for the probe during the biopsy 134 then the pre-calculation from the reference image of the images corresponding to the positions of the pre-calculated positions of the probe 135. More exactly, for each position supplied by the kinematic model, the reference image is re-sampled so that the resulting image corresponds to the reference image if it had been acquired in this position, within the limit of the available information in the reference image and without considering any deformation. The images are kept in the random access memory so as to enable a quick access subsequently. As a matter of fact, the calculated images and the corresponding transformation are stored in a list 136. This list of pre-calculated elements is used during the operation by the method of estimation of the transformation of the tracking image to the reference image 125, as illustrated in FIG. 9.

Figures 8A, 8B:
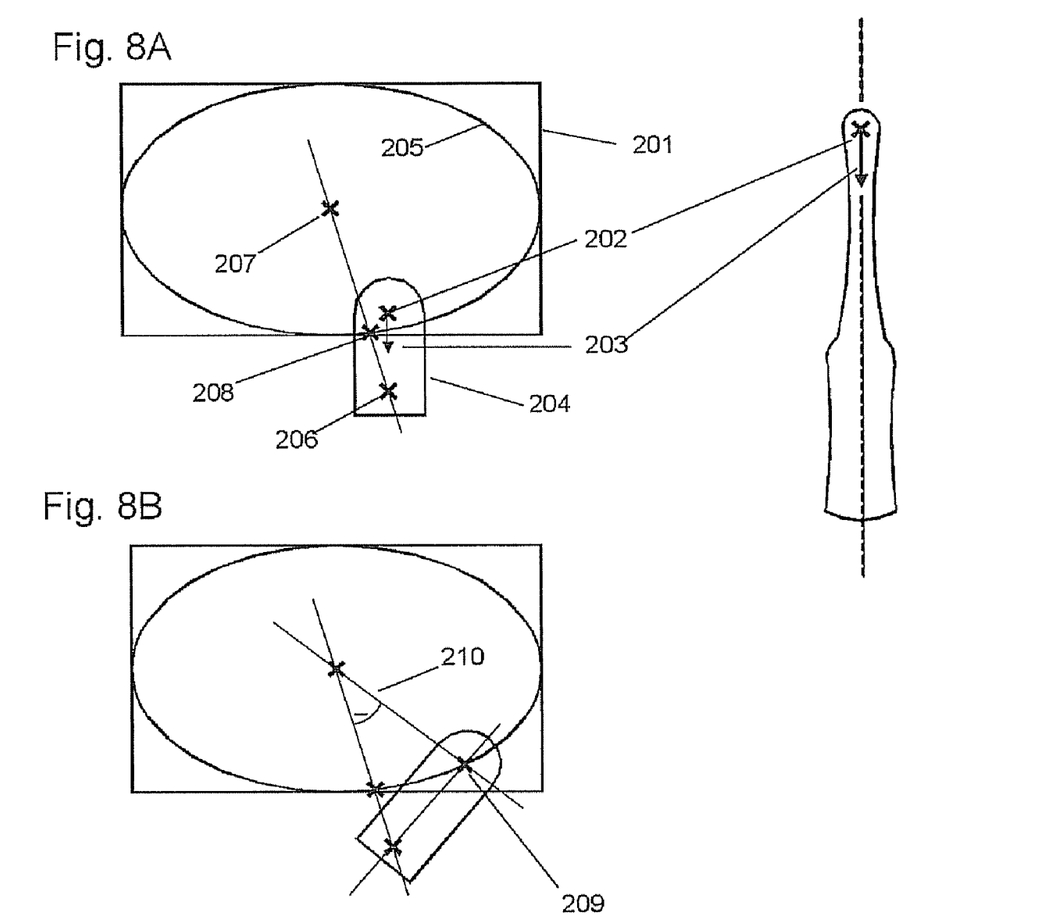
FIG. 8A shows the kinematic model of the probe with respect to the prostate in a first position of said probe.
FIG. 8B illustrates the kinematic model of the probe with respect to the prostate in a second position of said probe.
Figure 8C:
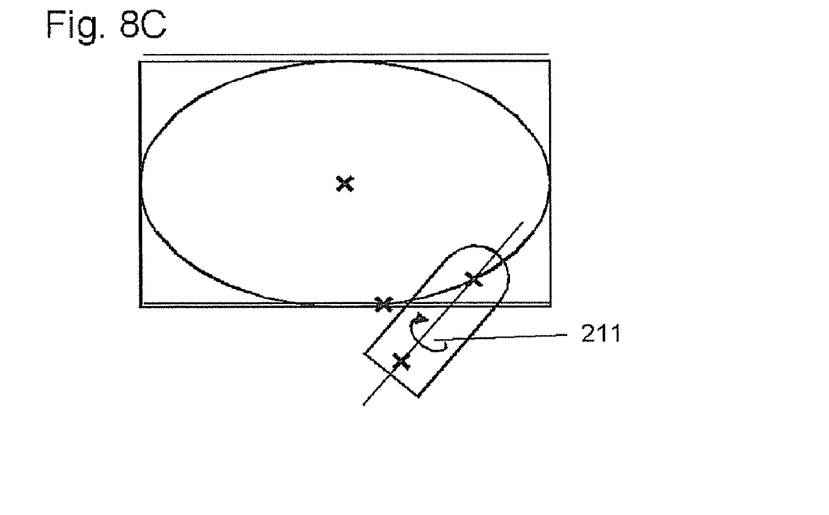
FIG. 8C illustrates the kinematic model of the probe with respect to the prostate in a third position of said probe.

The kinematic model is illustrated in FIGS. 8A, 8B and 8C. It is initialised 133 with an approximate surface of the prostate in the reference image 205 and a rotation point which uses an approximation of the rotational constraints of the probe in the rectum 206. It is also necessary to know the position of the ultrasonographic head with respect to the image it produces as represented for example by the centre 202 thereof, the orientation of the probe, still with respect to the image also called the "probe axis" 203 which can be represented by a vector pointed towards the handle of the probe. With such information, it is possible to estimate the position of the rectum with respect to the prostate and thus the region on the surface of the prostate which can be reached by the head of the probe. All the positions of the probe for which the head is in this region and for which the axis of the probe goes through the stationary rotation point is a correct approximation of all the positions of the probe which are physically possible during the positioning of the needle during a biopsy of the prostate. The approximation can be refined by modelising pressure fluctuations on the prostate by the clinician and varying the distance of the head to the surface by a few millimeters. Eventually, it should be made discrete as uniformly as possible for the whole position herabove. As an example, the method can be concretely implemented with an approximate prostatic surface biopsy 205 defined form a parallelepiped positioned by the clinician about the prostate visible in the reference image 201. The region which can be reached by the probe in the rectum is estimated from the point of intersection 208 of the line between the head of the probe 202 and the centre of the surface 207 with the surface passing through a polar representation of the ellipsoid 210 parameterised with alpha and beta angles 210 so that the point of intersection coincides with the representation for alpha and beta equal to zero. When limiting the absolute values of alpha and beta, a region is defined which shows an approximation of the part of the surface which can be reached by the head of the probe. All the positions for the probe for which the head is on the surface and the axis goes through the rotation point 206 can be sampled by following discretely alpha and beta parameters, each couple giving a contact point 210 and a third angle gamma 211 which is a model for the rotations of the probe about the axis 203 thereof.

Figure 9:
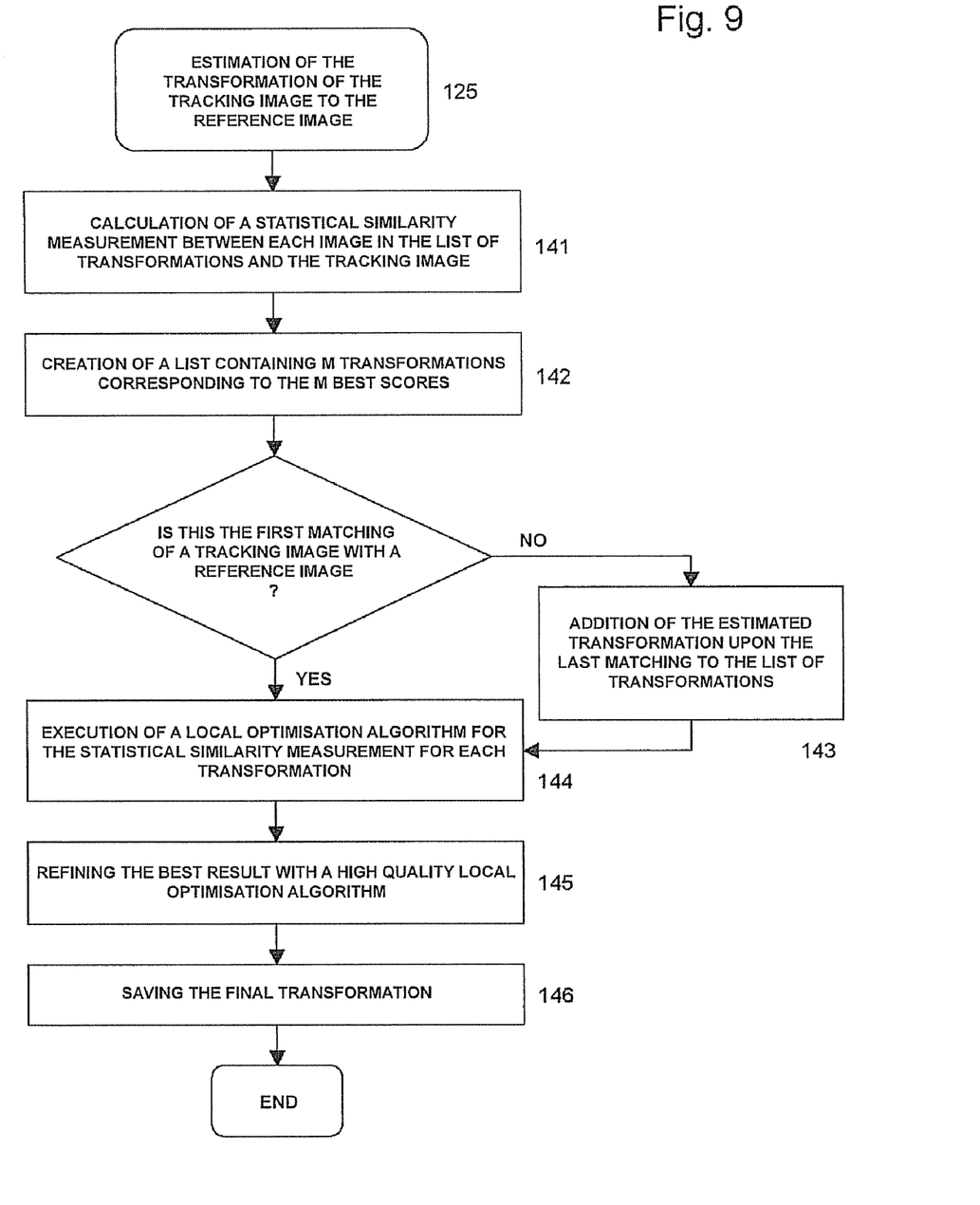
FIG. 9 is a diagram of the method for estimating the tracking image to the reference image.

FIG. 9 illustrates a method for estimating the transformation of the tracking image to the reference image 125 implemented during the acquisitions of biopsies 104. Starting from the estimation of the sampling path in the first image of the list, this method makes it possible to project the estimated path in the reference image. First, a statistic measure of the similarity is calculated between each image of the list of transformations and the tracking image 141. In an advantageous manner, the method is operated with a measure of the similarity of the "Pearson correlation" type, "standardised mutual information", "square distances sum" or "correlation ratio" type. Even more advantageously, it is possible to combine these or to combine the results of the application thereof on several aspects of the image such as the derivative or laplacian thereof. A list is then created 142, said list containing M transformations corresponding to the M best measurements of step 141. A correct robustness of the system is obtained with M=5. If the matching is the first matching of a tracking image of the reference image, the method goes through step 144. If the matching is not the first matching of a tracking image with the reference image and the estimated transformation upon the last matching is added to the list of M transformations 143 before going to the step 144. And for each transformation of the list, a local optimisation algorithm of the statistical measure of the similarity from such information is implemented 144. The object of the local optimisation 144 is to find the transformation which optimises the similarity in the neighbourhood of the initial transformation using a conventional local optimisation algorithm such as the Powell-Brent algorithm. Then, the best result obtained from the step 144 is refined with a high quality local optimisation algorithm 145. During such step, the same calculation as the one used during the step 144 is applied, but this time with parameters making it possible to obtain a finer accuracy for a longer calculation time. Then, the final transformation giving the best result for the statistical similarity and refined according to said high quality algorithm is recorded 146.

The present invention gives the practitioner a better possibility of treatment of cancer and potentially a quicker diagnostic and a more focused therapy. In addition, the medical and surgical treatments as well as convalescences can thus be shortened. The system also has an interest in the learning of the gesture. A young practitioner needs only be shown that the puncture was not carried out where it should have been and the training curve is accelerated.

As the endorectal prostate ultrasonography being is used for a certain number of therapeutic gestures often transperinal gestures (curietherapy, photodynamotherapy, cryotherapy), the present invention can be applied to therapeutic time. Then, the interest lies in that it gives the searcher or radiotherapist location information on therapeutic needles when and as they are inserted while complying with a prior operational planning. Then, when coupled with the integration of anatomic (regionalisation of the gland) or statistic (probable zones of presence of cancer) information or additional mode images (RIM, Doppler, elastrography, contrast image, CT, PET, fluorescence, etc) or results from previous operations on the same patient, the system can superimpose such new information with the reference ultrasonographic volume thus improving the planning and the guiding of the gesture.

The implementation of the imaging method can advantageously be assisted by software guiding the practitioner. Such software guides the practitioner in the succession of operations to be carried out in a linear way. Such software will first control the displaying of information relating to the preliminary sequence of acquisition of the reference image. It controls the means for entering the patient's information as well as, if need be, information relating to operations conditions (date, name of the operator, pre-operational information such as PSA or prostate volume, place of operation, etc.)

When all the compulsory information is recorded, the software controls the functionality relating to the acquisition of ultrasonographic images intended for the calculation of the reference image. When the quality of the reference image is validated by the operator or by an automatic processing, the software controls the following sequence corresponding to the sampling of biopsies. During this sequence, the software can record the ultrasonographic image acquired upon the triggering of a new sampling and visualise in real time a grouped image showing a superimposed reference image and path for the new sampling after the standardisation transformation.

When all biopsies have been carried out, the user controls the preparation of the report and the archiving of data. The processing of transformation of the acquired images to enable a superimposition on the reference image can be a transformation in the Cartesian space with the prostate being then assimilated to a solid object being subjected to no deformation during the sampling steps.

It is possible to improve the treatment with a non-linear transformation considering the deformation of the prostate between the condition at rest and the condition of prostate submitted to a local pressure by the ultrasonographic probe head as well as the action of the sampling needle. This system consists in recalculating an intermediate image of the prostate upon the sampling when minimising discrepancies between one area or identification points of the reference image and an area in the acquired image to match at its best a partial area to determine the identification points. This intermediate image corresponds to a change in the identification of the acquired image for optimising the superimposition with the reference image.

Then a second processing consists in deforming the acquired and thus repositioned image so as to match areas reference points of the acquired image with the reference image. The second transformation makes it possible to improve the quality of the superimposition and thus of the final representation of the superimposition of the biopsy paths and the reference image. In order to improve again the quality of such a superimposition, an advantageous solution consists in providing a recalculated acquired image validation step. Such validation can be carried out manually by the operator thus checking if the recalculated image is superimposed while it is visualised in a pertinent way on the reference image. Such verification is carried out with a three-dimensional visualisation, making it possible for the operator to explore in space the superimposition of images and carry out verifications under various orientations.

Such verification can be automatic using an evaluation processing of the discrepancies between the reference image and the recalculated image using the calculation of a measure of the similarity for automatically validating when the result of such measurement is lower than its threshold value. The measure of the similarity is estimated for each step during the phase convergence of the resetting method. The measurement function calculates, according to an exemplary implementation, the discrepancies between the canonical structures identified in the reference image and the acquired image for delivering at the end of the path an evaluation of the final discrepancies and thus the quality of the superimposition.

Another variant consists in integrating other previously or subsequently acquired images to superimpose these with the reference image and the biopsies path. Such other images are for example an MRI image of the prostate, an image from the anatomic model or a model from the statistic distribution of the tumoral areas or a series of images acquired on the same patient on different dates.

The invention claimed is:

1. A prostatic imaging method comprising recording and processing images acquired by an ultrasonographic head of a rectal probe equipped with an active puncture guide, processing at least a part of the images acquired by the probe for calculating transformations to a "reference image" repository relative to the initial position of a prostate, with at least a part of the images acquired during successive punctures including a location of various positions of a needle being recorded with a view to visualising representations thereof on a single image including at least a part of the prostate.

2. An imaging method according to the preceding claim, wherein the position of the sampling needle is visualised in the "reference image" repository or "tracking image" repository after the puncture, superimposed on an image of at least a part of the prostate showing the various positions of prior samplings.

3. An imaging method according to claim 1, wherein the position of the sampling needle is visualised in real time in the "reference image" repository or "tracking image" repository, being superimposed on an image of at least a part of the prostate showing the various positions of prior samplings.

4. An imaging method according to claim 1, further comprising tumoral distribution is visualised in the "reference image" repository after merging of a spatial distribution of the marked punctures with results from anatomopathologic analysis.

5. An imaging method according to claim 1, further comprising resetting a new prostatic image marked upon each new sampling.

6. An imaging system according to claim 1, further comprising a refreshing frequency of the images acquired by the ultrasonographic probe being at least 3 images per second.

7. An imaging method according to claim 1, further comprising using the ultrasonographic probe to give a three-dimensional image.

8. An imaging method according to claim 1, further comprising using the ultrasonographic probe to give a "2.5-dimensional" type image.

9. An imaging method according to claim 1, further comprising chronological marking with a serial number implementing means for the univocal labelling of each sampling area.

10. An imaging method according to claim 9, wherein the univocal labelling means are manually generated with the needle being in position.

11. An imaging method according to claim 9, wherein the univocal labelling means are generated by an automatic triggering of the acquisition of data through the capture of a sound, light, tactile or magnetic signal at the exact moment of biopsy sampling.

12. An imaging method according to claim 1, wherein the step of processing the acquired images further implements a kinematic model derived from anatomic constraints specific to a transrectal puncture of the prostate making it possible to identify probable positions of the probe during an operation.

13. An imaging system according to claim 1, wherein the step of processing the acquired images further implements the process of pre-calculating the probable positions of the probe during a biopsy and the images corresponding to the positions of the probe pre-calculated from the reference image.

14. An imaging method according to claim 1, wherein the step of processing the acquired images further implements an image resetting algorithm based on the local optimisation of a measure of the similarity.

15. An imaging method according to claim 1, further comprising using software for successively controlling the entering of a patient's information, a display of the information relative to a preliminary sequence of acquisition of the reference image, functionalities relating to the acquisition of the ultrasonographic images intended for the calculation of the reference image and when the quality of the reference image is validated by the operator or by an automatic processing, biopsies sampling sequence.

16. An imaging method according to claim 1, wherein the processing of the images consists of a non-linear transformation, taking into account a deformation of the prostate between a condition at rest and a condition of the prostate submitted to pressure.

17. An imaging method according to claim 1, further comprising validating a recalculated acquired image.

18. An imaging method according to the preceding claim, wherein the checking is automatised by a processing for evaluating discrepancies between the reference image and the recalculated image.

19. An imaging method according to the preceding claim, wherein the checking is automatised by a processing for evaluating the discrepancies between canonical structures registered in the reference image and the acquired image, so as to finally issue an estimation of the final discrepancies.

20. An imaging method according to claim 1, further comprising integrating other images previously or subsequently acquired to superimpose these on the reference image and biopsy paths.

21. A prostatic imaging system comprising a rectal probe and a calculator, with the probe including an ultrasonographic head for taking an image of a puncture area done with a needle actuated by an operator, with the calculator recording and processing the images acquired by the ultrasonographic head, the calculator also recording and processing images required by the probe in order to calculate transformations to a "reference image" repository relating to an initial position of a prostate, with at least a part of the images acquired during successive punctures including a location of various positions of the needle being recorded with a view to visualising representations thereof on a unique image including at least a part of the prostate.

22. A prostatic imaging system according to the preceding claim, further comprising a receptacle for collecting samples of tissues with an identifier correlated with a marking of a corresponding sampling area on a single image of the marked prostate.

23. A prostatic imaging system according to claim 21, wherein the rectal probe is a manually activated probe without any robotised positioning.

24. A prostatic imaging system according to claim 21, wherein the rectal probe is a manually activated probe moved by an optical or magnetic locator.

25. A prostatic imaging system according to claim 21, wherein the rectal probe is a probe positioned by a robot.

26. A non-transitory computer medium including recording of a calculator controlling program for the implementation of prostatic imaging, the computer medium comprising programming instructions recording and processing images acquired by an ultrasonographic head of a rectal probe equipped with an active puncture guide, processing at least a part of the images acquired by the probe for calculating transformations to a "reference image" repository relative to the initial position of a prostate, with at least a part of the images acquired during successive punctures including a location of various positions of a needle being recorded with a view to visualizing representations thereof on a single image including at least a part of the prostate.

* * * * *